United States Patent
Doron et al.

(10) Patent No.: US 11,995,849 B2
(45) Date of Patent: May 28, 2024

(54) AUTOMATIC REGISTRATION OF AN ANATOMICAL MAP TO A PREVIOUS ANATOMICAL MAP

(71) Applicant: BIOSENSE WEBSTER (ISRAEL) LTD., Yokneam (IL)

(72) Inventors: Itai Doron, Katsir (IL); Fady Massarwa, Baka Al Gharbiyya (IL); Assaf Cohen, Kiryat Bialik (IL); Natan Sharon Katz, Atlit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 413 days.

(21) Appl. No.: 17/328,043

(22) Filed: May 24, 2021

(65) Prior Publication Data

US 2022/0375108 A1    Nov. 24, 2022

(51) Int. Cl.
 G06T 7/33     (2017.01)
 A61B 18/14    (2006.01)
 A61B 18/00    (2006.01)

(52) U.S. Cl.
 CPC ............ *G06T 7/33* (2017.01); *A61B 18/1492* (2013.01); *A61B 2018/00577* (2013.01); *G06T 2207/20101* (2013.01); *G06T 2207/20212* (2013.01); *G06T 2207/30048* (2013.01)

(58) Field of Classification Search
 CPC .. H05K 7/2039; H01R 13/516; G02B 6/4269; G02B 6/4278
 See application file for complete search history.

(56) References Cited

U.S. PATENT DOCUMENTS

| | | | | |
|---|---|---|---|---|
| 10,307,619 B2* | 6/2019 | Levy | ......................... | G06T 7/74 |
| 10,512,792 B2* | 12/2019 | Kumar | ................. | A61N 5/1031 |
| 2005/0197568 A1 | 9/2005 | Vass | | |
| 2008/0020362 A1* | 1/2008 | Cotin | ................... | G09B 23/285 |
| | | | | 434/267 |
| 2011/0026794 A1 | 2/2011 | Sundar | | |
| 2019/0271771 A1* | 9/2019 | Lieblich | ............... | G06V 10/267 |
| 2019/0318484 A1* | 10/2019 | Dougherty | ................ | G06T 7/11 |
| 2020/0316850 A1* | 10/2020 | Seitz | ...................... | G09B 23/30 |

FOREIGN PATENT DOCUMENTS

WO    WO2020224744 A1    11/2020

OTHER PUBLICATIONS

European Search report for corresponding EPA No. 22174849.4 dated Nov. 3, 2022.

(Continued)

*Primary Examiner* — Dhaval V Patel

(57) ABSTRACT

A method includes calculating a first medial-axis tree graph of a volume of an organ of a patient in a first computerized anatomical map of the volume, acquired at a first time. A second medial-axis tree graph is calculated, of a volume of the organ of the patient in a second computerized anatomical map of the volume, acquired at a second time that is different from the first time. A deviation is detected and estimated, between the first and second tree-graphs. Using the estimated deviation, the first and second medial-axis tree graphs are registered with one another. Using the registered first and second tree graphs, the first and second computerized anatomical maps are combined.

15 Claims, 3 Drawing Sheets

(56) References Cited

OTHER PUBLICATIONS

Thiran J-P et al: "Morphological Registration of 3D Medical Images", Proceedings of the International Conference on Image Processing (ICIP) Lausanne, Sep. 16-19, 1996; [Proceedings of the International Conference on Image Processing (ICIP)], New York, IEEE, US, Sep. 16, 1996, pp. 253-256, XP000733249.
Porras Antonio R et al: "Pre to Intraoperative Data Fusion Framework for Multimodal Characterization of Myocardial Scar Tissue", IEEE Journal of Translational Engineering in Health and Medicine, vol. 2, Sep. 4, 2014, pp. 1-11, XP011559007.

* cited by examiner

AUTOMATIC REGISTRATION OF AN ANATOMICAL MAP TO A PREVIOUS ANATOMICAL MAP

FIELD OF THE INVENTION

The present invention relates generally to cardiac mapping, and particularly to registration of anatomical cardiac maps.

BACKGROUND OF THE INVENTION

Registration methods of organ visualizations were previously proposed in the patent literature. For example, U.S. Patent Application Publication No. 2005/0197568 describes a method for registration of cardiac image data in an interventional system. The method includes inserting a first plurality of fiducial points on an acquired 3D anatomical image and exporting the 3D anatomical image, with the first plurality of inserted fiducial points thereon, to an interventional system. A second plurality of fiducial points is inserted on the exported 3D anatomical image using the interventional system, and the first and said second plurality of fiducial points are aligned to one another so as to register the exported 3D anatomical image with the interventional system.

As another example, U.S. Patent Application Publication No. 2011/0026794 describes a method for performing deformable non-rigid registration of 2D and 3D images of a vascular structure for assistance in surgical intervention, that includes acquiring 3D image data. An abdominal aorta is segmented from the 3D image data using graph-cut based segmentation to produce a segmentation mask. Centerlines are generated from the segmentation mask using a sequential topological thinning process. Three-dimensional graphs are generated from the centerlines. Two-dimensional 2D image data is acquired. The 2D image data is segmented to produce a distance map. An energy function is defined based on the 3D graphs and the distance map. The energy function is minimized to perform non-rigid registration between the 3D image data and the 2D image data. The registration may be optimized.

SUMMARY OF THE INVENTION

An embodiment of the present invention that is described herein provides a method including calculating a first medial-axis tree graph of a volume of an organ of a patient in a first computerized anatomical map of the volume, acquired at a first time. A second medial-axis tree graph is calculated, of a volume of the organ of the patient in a second computerized anatomical map of the volume, acquired at a second time that is different from the first time. A deviation is detected and estimated, between the first and second tree-graphs. Using the estimated deviation, the first and second medial-axis tree graphs are registered with one another. Using the registered first and second tree graphs, the first and second computerized anatomical maps are combined.

In some embodiments, detecting the deviation includes identifying movement of one or more landmarks between the first and second computerized anatomical maps.

In some embodiments, the landmarks include one or both of a coronary sinus catheter and a body surface patch.

In an embodiment, detecting the deviation includes detecting a discontinuity between corresponding edge points of the first and second medial-axis tree graphs.

In another embodiment, detecting and estimating the deviation includes detecting and estimating a displacement between the first and second tree-graphs.

In some embodiments, combining the first and second computerized anatomical maps includes generating a continuous anatomical map of the volume.

In some embodiments, the method according further includes estimating two or more deviations between three or more tree-graphs calculated in three or more respective anatomical maps. Using the estimated deviations, the three or more tree graphs are registered with one another. Using the registered tree graphs, the three or more anatomical maps are combined.

In an embodiment, the method further includes presenting the combined anatomical map to a user.

In some embodiments, combining the first and second computerized anatomical maps includes combining at least a first ablation location in the first anatomical map and a second ablation location in the second anatomical map.

There is additionally provided, in accordance with another embodiment of the present invention, a system including a processor and a monitor. The processor is configured to calculate a first medial-axis tree graph of a volume of an organ of a patient in a first computerized anatomical map of the volume, acquired at a first time, to calculate a second medial-axis tree graph of a volume of the organ of the patient in a second computerized anatomical map of the volume, acquired at a second time that is different from the first time, to detect and estimate a deviation between the first and second tree-graphs, to register the first and second medial-axis tree graphs with one another using the estimated deviation, and, using the registered first and second tree graphs, to combine the first and second computerized anatomical maps. The monitor is configured to display the combined first and second computerized anatomical maps to a user.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
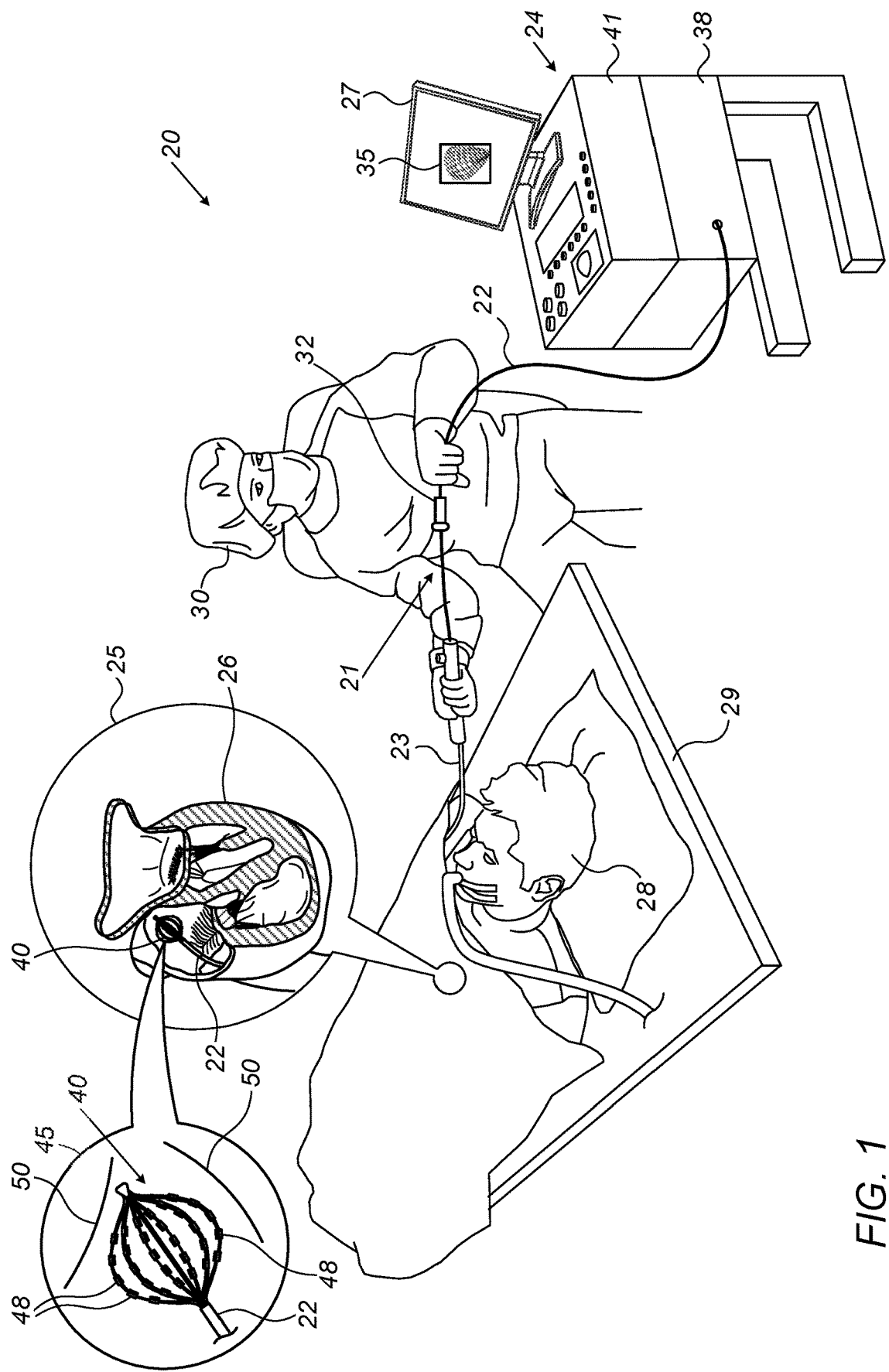
FIG. 1 is a schematic, pictorial illustration of a system for electro-anatomical mapping and ablation, in accordance with an exemplary embodiment of the present invention.

Catheter-based anatomical mapping techniques may produce a computerized anatomical map of a cavity (e.g., surface of a volume) of an organ. Such a map may be subsequently used in performing an ablation. For example, a cardiac mapping system may generate a map of a cardiac chamber, such as the left atrium (LA), to be used in ablation of ostia of pulmonary veins (PV), in order to treat atrial fibrillation.

However, during the invasive procedure that involves mapping and ablating the pulmonary veins, the patient may move and cause a map shift. While the mapping and ablating may be continued, a new map needs to be registered to the previous map to understand where the earlier ablations occurred.

To overcome this problem, physicians sometimes initially register their maps to a CT or MRI image. In this case, when there is a map shift, the physicians can re-register the new map to the CT/MR image, so that both maps are registered. However, such an initial registration is manual, time-consuming, and dependent on how well a physician identifies points to be used for the registration.

Some embodiments of the present invention that are described hereinafter provide methods for generating a skeleton of the cardiac chamber as the procedure (mapping and ablating) is being performed. In these embodiments, a processor receives an anatomically mapped volume of a cardiac chamber (e.g., of a LA) of a heart. In case of an LA, the processor automatically identifies the PVs and the appendage-opening regions on the anatomical map of the LA. To this end, the processor computes a medial axis graph (also called hereinafter, in brief, a "skeleton") from the anatomical map. A point on a medial axis of a volume can be defined as a point in a planar cross-section of the volume having more than one closest point on a resulting boundary in 2D in the cross-sectional plane. Originally referred to as a "topological skeleton," it was introduced in 1967 as a tool for biological shape recognition.

A method of generating a skeleton is described in U.S. patent application Ser. No. 17/009,715, titled "Automatic Identification and Processing of Anatomical Structures in an Anatomical Map," filed Sep. 1, 2020, whose disclosure is incorporated herein by reference. The processor may use this method, or any other suitable method, for generating the medial axis graph ("skeleton").

Such a skeleton may aid the physician to perform a subsequent ablation of a PV by removing irrelevant electrophysiological (EP) information that may be confusing, such as electrical activity appearing in an electrophysiological (EP) version of the map, for example, in a form of map coloring, due to a PV not being removed from the map. This EP information, which is already considered irrelevant just before performing an ablation, may cause the physician to erroneously place an ablating catheter too deep into that PV (e.g., rather than placing the catheter at the ostium of the PV).

In an embodiment of the present invention, if there is patient movement, which is typically identified by shifting of landmarks such as a coronary sinus catheter or body surface patches, the procedure is continued and a new skeleton is generated. The processor identifies end points of the two skeletons, e.g., centers of the pulmonary veins, and these end points are used to register the before-movement and after-movement maps. As noted above, some embodiments of the disclosed technique provide methods to use skeleton registration to combine an existing portion of map (e.g., portion before patient motion) with a map portion made after motion, in order to generate an updated patient-motion compensated (e.g., continuous) map.

The processor uses the skeleton registration to automatically generate a patient-motion compensated anatomical map. To this end, in an embodiment, the processor calculates a first medial-axis tree graph of a volume of an organ of a patient in a first computerized anatomical map of the volume, acquired at a first time. The processor then calculates a second medial-axis tree graph of a volume of the organ of the patient in a second computerized anatomical map of the volume, acquired at a second time that is different from the first time.

This second time may be after the patient has moved, during the same session or during a subsequent session. Either way, the processor detects, using means described below, and estimates, a deviation between the first and second tree-graphs.

Using the estimated deviation, the processor registers the first and second medial-axis tree graphs with one another, and combines the first and second computerized anatomical maps using the registered tree graph.

In one embodiment, the processor detects the deviation by identifying movement of one or more landmarks between the first and second computerized anatomical maps. The landmarks may comprise one or more of a coronary sinus catheter and a body surface patch.

In another embodiment, the processor detects the deviation by detecting an unexpected discontinuity between two edge points of the first and second medial-axis tree graphs.

The method described above may be applied to estimate two or more displacements deviations between three or more tree-graphs. Using the registered tree graphs, the processor may combine three or more anatomical maps.

In some embodiments, combining the first and second computerized anatomical maps comprises combining ablation locations (e.g., actual ablation lesions or planned locations) from the first and second anatomical maps. This technique allows, in one embodiment, visualizing ablation lesions that were formed before the movement, on the registered map produced after the movement. In this manner the physician is able to apply the desired ablation pattern regardless of the patient movement.

In another embodiment, the patient movement is identified by the processor that constructs the tree graph by identifying one or more incorrect tree graph edge points (e.g., edge points of the tree graph that should not exist but occur due to a discontinuity). The processor further estimates a deviation (e.g., size and direction of discontinuity due to displacement) between portions of the tree graph by estimating a displacement between their respective edge points. In general, a deviation may be a non-uniform and include, position dependent displacement and/or rotation and/or stretch and/or contraction.

In contrast to the physician registration method using a medical image, using skeletons requires no such image (or registration to such an image). In addition, the method described hereafter is completely automatic.

Typically, the processor is programmed in software containing a particular algorithm that enables the processor to conduct each of the processor-related steps and functions outlined above.

The disclosed registration technique may ease the work required by a physician in analyzing an anatomical map during an invasive procedure. The disclosed technique may thus make the clinical diagnosis and subsequent treatment, such as catheter ablation, safer and more efficient.

System Description

FIG. 1 is a schematic, pictorial illustration of a system for electro-anatomical mapping and ablation 20, in accordance with an embodiment of the present invention.

System 20 comprises a catheter 21, having a shaft 22 that is navigated by a physician 30 into a heart 26 of a patient 28 lying on a table 29. In the pictured example, physician 30 inserts shaft 22 through a sheath 23, while manipulating the distal end of shaft 22 using a manipulator 32 near the proximal end of the catheter and/or deflection from the sheath 23. As shown in an inset 25, basket catheter 40 is fitted at the distal end of shaft 22. Basket catheter 40 is inserted through sheath 23 in a collapsed state and is then expanded within heart 26.

In an embodiment, basket catheter 40 is configured to (i) perform spatial mapping of a cardiac chamber of heart obtaining electrophysiological signals from cardiac chamber surfaces 50, and (ii) apply electrical ablative energy to cardiac chamber surfaces 50. An inset 45 shows basket catheter 40 in an enlarged view, inside a cardiac chamber of heart 26. As seen, basket catheter 40 comprises an array of electrodes 48 coupled onto splines that form the basket shape. In one embodiment, the ablation is performed by applying ablative energy between pairs of electrodes 48, in a bi-polar ablation mode.

The proximal end of catheter 21 is connected to a console 24. Console 24 comprises a processor 41, typically a general-purpose computer, with suitable front end and interface circuits 38 for transmitting and receiving electrical signals to and from catheter 21, as well as for controlling the other components of system 20. In an embodiment, the surface of the surrounding anatomy is presented to physician 30 on a monitor 27, e.g., in a graphical form of a mesh diagram 35.

Processor 41 is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Although the illustrated exemplary embodiment in FIG. 1 relates specifically to the use of a basket catheter for cardiac mapping, other distal-end assemblies may be used, such as In particular, processor 41 runs a dedicated algorithm as disclosed herein, including in FIG. 3, that enables processor 41 to perform the disclosed steps, as further described below.

Automatic Registration of Anatomical Map Portions

Figure 2:
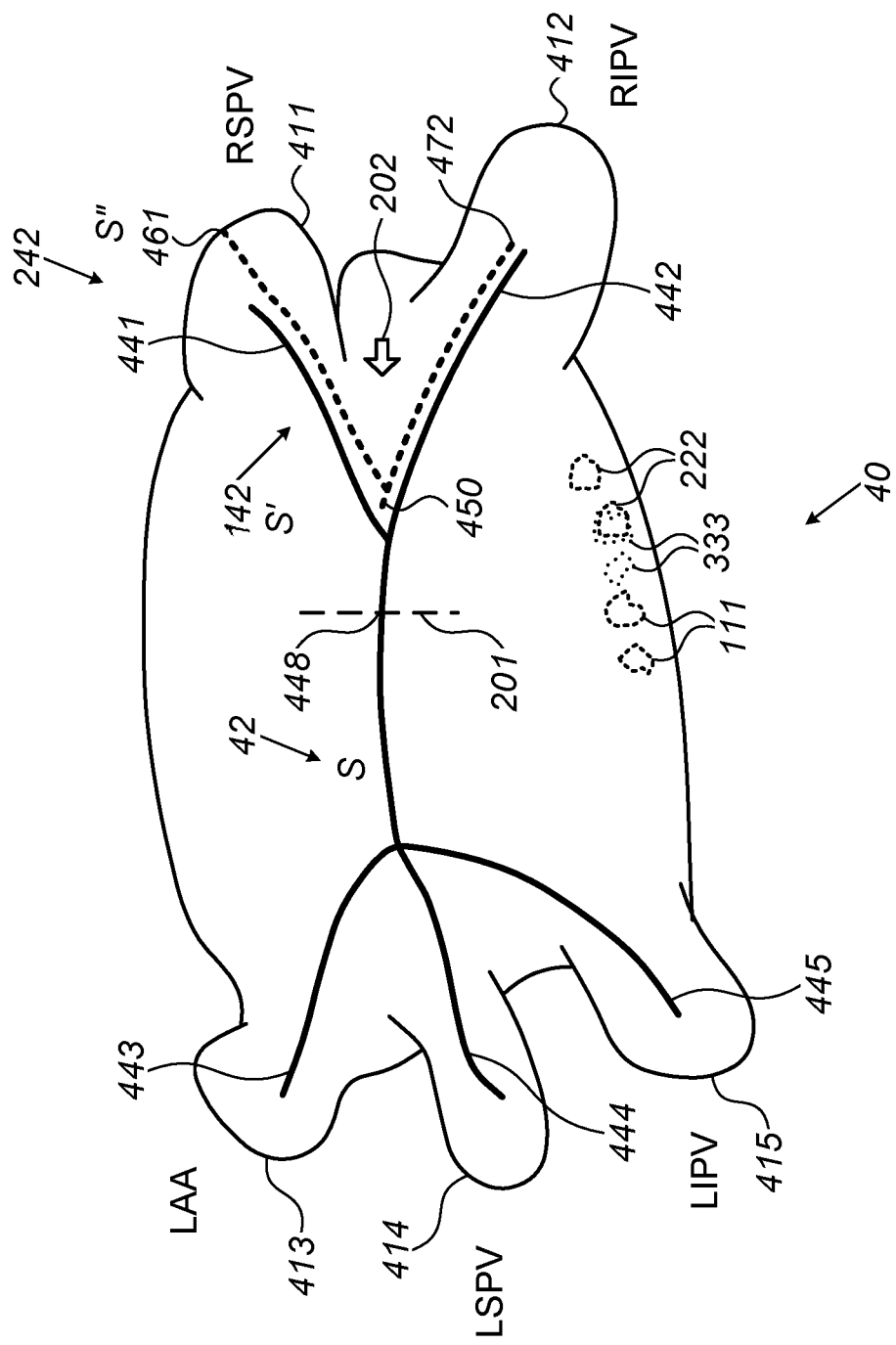
FIG. 2 is a schematic, pictorial volume rendering of an automatically generated patient-motion compensated anatomical map of a left atrium using map-skeleton registration, in accordance with an exemplary embodiment of the present invention.

FIG. 2 is a schematic, pictorial volume rendering of an automatically generated patient-motion compensated anatomical map 40 of a left atrium using map-skeleton registration, in accordance with an embodiment of the present invention.

As seen, for user convenience, surface mesh map 40 is rotated (by processor 41) to a posterior-anterior (back to front) PA orientation, so that the right of the view corresponds to the right side of the viewer, and the left of the view is at the left side of the patient. FIG. 2 further exemplifies automatically identified pulmonary veins (PVs) 411-412 and 414-415.

In the depicted embodiment, before the patient moved, processor 41 computed a "medial axis" skeleton portion S 42 from LA surface anatomical map 35. Skeleton portion 42 (i.e., the tree graph) comprises three major branches 413-415 out of the five major branches (N=5), branches 441-445. That is, out of branches 441-445, branches 443-445 were generated before the patient began to move, which occurred during a point 201 as the skeleton was still being generated.

As a result of patient movement, the generation of the remainder of the skeleton (i.e., portion S",242) is shifted. In the illustrated embodiment, processor 41 identifies edge points, such as end point 448 of skeleton portion 42, and begin point 450, and end points, 461, and 472 of the skeleton portions 242. Using the begin points and end points, processor 41 registers (seen schematically by arrow 202) the before-movement and after-movement map skeleton portions (i.e., creates a motion-compensated skeleton portion S', 142). The processor uses the skeleton registration to automatically generate a patient-motion compensated anatomical map. For example, the processor applies a transformation, defined by the registration of the two skeleton portions, to register the after-movement map with the before-movement map portions with each other.

In another embodiment, where a skeleton was completed before the patient moved, the algorithm may use more end points, such as of an available old version of branches 441 and 442.

As seen in FIG. 2, lesions 111 were mapped before patient movement (at a point 201). As a result of the motion, locations 111 are displaced relative to planned ablation locations 333. Using registration of the two map portions, lesions 333 are shifted to locations 222, to form a consistent path of ablation lesions (111, 222). Note that, depending on the reference map in use, a consistent path of ablation lesions (111—shifted, 333) may be made, by displacing locations 111 instead. The example schematic volume rendering shown in FIG. 2 is chosen purely for the sake of conceptual clarity. For example, if multiple skeleton portions occur (i.e., three or more) due to patient motion, processor 41 will register all of them to generate a patient-motion compensated map.

Figure 3:
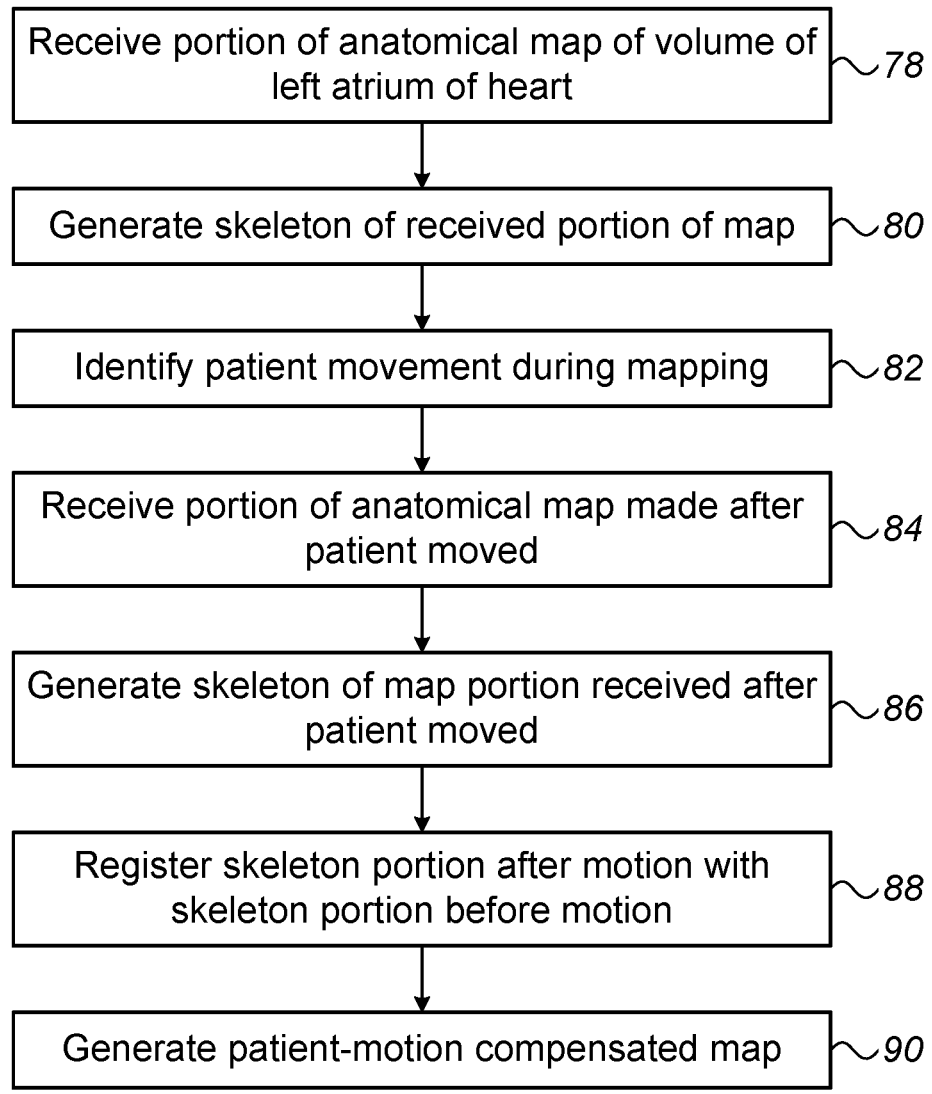
FIG. 3 is a flow chart that schematically illustrates an automatic method of generating the patient-motion compensated anatomical map of FIG. 2 using map-skeleton registration, in accordance with an exemplary embodiment of the present invention.

FIG. 3 is a flow chart that schematically illustrates an automatic method of generating the patient-motion compensated anatomical map 40 of FIG. 2 using map-skeleton registration, in accordance with an embodiment of the present invention. The algorithm according to the presented embodiment carries out a process that begins at a before map portion receiving step 78, with processor 41 receiving a portion of anatomical map 40 made before patient movement. In the shown case it is a map portion of a left atrium.

Next, in skeleton portion generation step 80, the processor generates a skeleton 42 of the before portion of the map.

In a motion identification step 82, processor 41 identifies an open-ended point 448 on skeleton 42 that corresponds an event in which the patient moved. The processor may identify patient movement using landmarks of at least one of a coronary sinus catheters and body surface patches. In another embodiment, the patient movement is identified by the processor that constructs the tree graph by identifying two edge points (448, 450) of a tree graph that should not be such (e.g., due to discontinuity).

At an after-movement map portion receiving step 84, processor 41 receives a portion of anatomical map 40 made after the patient moved. At skeleton portion generation step 86, the processor generates a skeleton 242 of the after-movement portion of the map.

The processor registers the after-movement portion skeleton with the previous portion skeleton, at a skeleton registration step 88 (i.e., creates a motion-compensated skeleton portion S', 142). For example, the processor uses end point 448 and begin point 450, as well as using end points 461 and 472, to perform the registration.

Finally, using the registration, the processor combines the before-movement and after-movement map portions to generate a patient-motion compensated (e.g., artifact free) map 40.

The example flow chart shown in FIG. 3 is chosen purely for the sake of conceptual clarity. In optional embodiments, various additional steps may be performed, for example to automatically register, with medical images, the openings into the LA of the PVs that are identified to be cut off of the motion compensated map.

Although the embodiments described herein mainly address cardiac applications, the methods and systems described herein can also be used in other applications. For example, the disclosed method may be utilized to register an otolaryngologic map.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for automatic registration of an anatomical map to a previous anatomical map, the method comprising:
calculating a first medial-axis tree graph of a volume of an organ of a patient in a first computerized anatomical map of the volume, acquired at a first time;
calculating a second medial-axis tree graph of a volume of the organ of the patient in a second computerized anatomical map of the volume, acquired at a second time that is different from the first time;
detecting and estimating a deviation between the first and second tree-graphs;
using the estimated deviation, registering the first and second medial-axis tree graphs with one another; and
using the registered first and second tree graphs, combining the first and second computerized anatomical maps, wherein combining the first and second computerized anatomical maps comprises generating a continuous anatomical map of the volume.

2. The method according to claim 1, wherein detecting the deviation comprises identifying movement of one or more landmarks between the first and second computerized anatomical maps.

3. The method according to claim 2, wherein the landmarks comprise one or both of a coronary sinus catheter and a body surface patch.

4. The method according to claim 1, wherein detecting the deviation comprises detecting a discontinuity between corresponding edge points of the first and second medial-axis tree graphs.

5. The method according to claim 1, wherein detecting and estimating the deviation comprises detecting and estimating a displacement between the first and second tree-graphs.

6. The method according to claim 1, and comprising:
estimating two or more deviations between three or more tree-graphs calculated in three or more respective anatomical maps;
using the estimated deviations, registering the three or more tree graphs with one another; and
using the registered tree graphs, combining the three or more anatomical maps.

7. The method according to claim 1, and comprising presenting the combined anatomical map to a user.

8. The method according to claim 1, wherein combining the first and second computerized anatomical maps comprises combining at least a first ablation location in the first anatomical map and a second ablation location in the second anatomical map.

9. A system for automatic registration of an anatomical map to a previous anatomical map, the system comprising:
a processor, which is configured to:
calculate a first medial-axis tree graph of a volume of an organ of a patient in a first computerized anatomical map of the volume, acquired at a first time;
calculate a second medial-axis tree graph of a volume of the organ of the patient in a second computerized anatomical map of the volume, acquired at a second time that is different from the first time;
detect and estimate a deviation between the first and second tree-graphs;
using the estimated deviation, register the first and second medial-axis tree graphs with one another; and
using the registered first and second tree graphs, combine the first and second computerized anatomical maps;
wherein, in combining the first and second computerized anatomical maps, the processor is configured to generate a continuous anatomical map of the volume; and
a monitor, which is configured to display the combined first and second computerized anatomical maps to a user.

10. The system according to claim 9, wherein the processor is configured to detect the deviation by identifying movement of one or more landmarks between the first and second computerized anatomical maps.

11. The system according to claim 10, wherein the landmarks comprise one or both of a coronary sinus catheter and a body surface patch.

12. System according to claim 9, wherein the processor is configured to detect the deviation by detecting a discontinuity between corresponding edge points of the first and second medial-axis tree graphs.

13. The system according to claim 9, wherein the processor is configured to detect and estimate the deviation by detecting and estimating a displacement between the first and second tree-graphs.

14. The system according to claim 9, wherein the processor is further configured to:
estimate two or more deviations between three or more tree-graphs calculated in three or more respective anatomical maps;
using the estimated deviations, register the three or more tree graphs with one another; and
using the registered tree graphs, combine the three or more anatomical maps.

15. The system according to claim 9, wherein, in combining the first and second computerized anatomical maps, the processor is configured to combine at least a first ablation location in the first anatomical map and a second ablation location in the second anatomical map.

* * * * *